(12) United States Patent
Pang

(10) Patent No.: US 6,399,058 B1
(45) Date of Patent: Jun. 4, 2002

(54) METHODS FOR TREATING OCULAR DISEASES

(75) Inventor: Iok-Hou Pang, Grand Prairie, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/486,854

(22) PCT Filed: Aug. 18, 1998

(86) PCT No.: PCT/US99/17098

§ 371 (c)(1), (2), (4) Date: Mar. 3, 2000

(87) PCT Pub. No.: WO99/13868

PCT Pub. Date: Mar. 25, 1999

Related U.S. Application Data

(60) Provisional application No. 60/059,167, filed on Sep. 17, 1997.

(51) Int. Cl.[7] ............. A01N 63/00; A01N 65/00
(52) U.S. Cl. ......................... 424/93.7
(58) Field of Search .......... 424/93.7; 435/240.2, 435/240.22, 244; 514/912, 250, 210, 449, 886, 825

(56) References Cited

U.S. PATENT DOCUMENTS

| | | | |
|---|---|---|---|
| 5,500,230 A | * | 3/1996 | Nathanson et al. |
| 5,550,050 A | * | 8/1996 | Holland et al. |
| 5,641,749 A | * | 6/1997 | Yan et al. |
| 5,904,144 A | * | 5/1999 | Hammang et al. |

FOREIGN PATENT DOCUMENTS

| | | |
|---|---|---|
| WO | WO 95/28166 | 10/1995 |
| WO | WO 95/34302 | * 12/1995 |
| WO | WO 97/34586 | 9/1997 |

OTHER PUBLICATIONS

Yousufzai et al., Expermental Eye Research, 65(1), 78–81. Endothelin–1 stimulates the release of arachidonic acid and prostaglandins in cultured human ciliary muscle cells; activation of phospholipase A2.*

Nathanson, Investigative Ophthalmology & Visual Science, 28(8), 1357–64. Atropetom–activated guanylate cyclase in the anterior segment. Identification, localization, and effects of atriopeptins on IOP.*

Misawa et al., J Neurochem., 62: 465–470. Calcium–independent release of acetycholine from stable cell lines expressing mouse choline acetyltransferase cDNA.*

Yousufzai et al., Expermental Eye Research, 65(1), 78–81. Endothelin–1 stimulates the release of arachidonic acid and prostaglandins in cultured human ciliary muscle cells; activation of phospholipase A2, Jul. 1997.*

Nathanson, Investigative Ophthalmology & Visual Science, 28(8), 1357–64. Atropetom–activated guanylate cyclase in the anterior segment. Identification, localization, and effects of atriopeptins on IOP, Aug. 1997.*

Misawa et al., J Neurochem., 62:465–470. Calcium–independent release of acetycholine from stable cell lines expressing mouse choline acetyltransferase cDNA, 1994.*

Yousufzai, et al. Experimental Eye Research, 65(1), 73–81. Endothelin–1 stimulates the release of arachidonic acid and prostaglandins in cultured human ciliary muscle cells: activation of phospholipase A2, Jul. 1997.*

Nathanson. Investigative Ophthalmology & Visual Science, 28(8), 1357–64. Atriopeptin–activated guanylate cyclase in the anterior segment. Identification, localization, and effects of atriopeptins on IOP, Aug. 1987.*

Misawa et al. J Neurochem., 62: 465–470. Calcium–indepenent release of acetylcholine from stable cell lines expressing mouse choline acetyltransferase cDNA, 1994.*

MacCumber, et al., "Ocular Effects of the Endothelins, Abundant Peptides in the Eye" *Arch Ophthalmology.*, vol. 109:705–709, 1991.

Martindale—The Extra Pharmacopoeia 31st Edition, 1996, Royal Pharmaceutical Society, p. 1414, col. 2, p. 1415, col. 3.

* cited by examiner

*Primary Examiner*—Christopher R. Tate
*Assistant Examiner*—Michele C. Flood
(74) *Attorney, Agent, or Firm*—Sally S. Yeager

(57) ABSTRACT

Methods, for lowering intraocular pressure by implanting in the anterior chamber encapsulated cells which secrete an intraocular pressure lowering substance.

2 Claims, No Drawings

METHODS FOR TREATING OCULAR DISEASES

This application claims the benefit of provisional application No. 60/059,167 filed Sep. 17, 1997

The present invention is directed to methods for treating ocular diseases by implanting capsules in the eye which contain cells that secrete therapeutic amounts of pharmaceuticals to treat ocular diseases such as glaucoma.

BACKGROUND OF THE INVENTION

Primary open angle glaucoma is a family of ocular diseases with characteristic cupping of the optic nerve head and eventual loss of visual field due to pathological changes at the optic nerve head and retina. One of the several risk factors for glaucoma is an increase in intraocular pressure (IOP). It is generally believed that reduction of TOP by pharmacological agents can delay or prevent the development of glaucomatous optic retinopathy (Perkins, "Treatment of Glaucoma by Lowering Intraocular Pressure," Glaucoma, (eds.) P. L. Kaufman and T. W. Mittag, Mosby Publishing Co., pp. 9.1–9.6, 1991).

The current invention describes novel methods for the treatment of glaucoma in human patients. These methods, include the implantation into the eye of encapsulated cells that naturally or are bioengineered to secrete continuously appropriate compounds for the treatment of ocular hypertension.

The implantation of capsules containing cells that secrete biologically active molecules is known. For example, WO 95/05452 discloses compositions and methods for delivery of biologically active molecules using genetically altered cells in capsules. WO 95.8166 discloses a method for implanting encapsulated cells in a host, including preparing the cells for implantation by exposing them to the restrictive conditions that match the implantation site. WO 9/0264A2 discloses a method for controlling growth of cells which are encapsulated in a bioartificial organ (BAO). The publication further discloses a method whereby cells are proliferated in vitro and a balance between proliferation and differentiation is controlled when the cells are encapsulated in a BAO. The method allows for regulation of cell numbers in the BAO and, therefore improved regulation of their output. The method also discloses control of the cell location in the BAO thereby reducing undesirable necrotic cell cores in the BAOs. WO94/25503 discloses certain graft polymers for use in the encapsulation of living cells. WO 94/10950 discloses microporous capsules useful as an implantation device for cell therapy. U.S. Pat. No. 5,158,881 discloses a method and system for encapsulating cells within a semi-permeable polymeric membrane by co-extruding an aqueous cell suspension and a polymeric solution through a common port to form a tubular extrudate having a polymeric outer coating which encapsulates the cell suspension. U.S. Pat. No. 5,283,187 also discloses a method for encapsulating living cells within a semipermeable polymeric membrane by co-extruding an aqueous cell suspension and a polymeric solution through a common port having at least one concentric bore to form a tubular extrudate having a polymeric membrane which encapsulates the cell suspension. WO 95/01203 discloses an apparatus and method for sealing implantable hollow fiber encapsulation devices.

None of the cited publications disclose the use of the capsules containing secreting cells for implantation into an eye to treat glaucoma.

SUMMARY OF THE INVENTION

This invention relates to novel methods for implanting encapsulated cells in a glaucomatous eye of a patient. The encapsulated cells produce therapeutic amounts of one or more pharmacologically active substances which may be useful in lowering intraocular pressure.

DESCRIPTION OF PREFERRED EMBODIMENTS

The present invention is directed to the use of capsules which are permeable to nutrients, but isolate encapsulated cells from the immune defense systems of its host. The encapsulated cells naturally or are bioengineered to continuously secrete therapeutic amounts of pharmaceuticals useful to treat ocular conditions.

The manufacture of spherical or tubular capsules has been disclosed in previous patents, such as U.S. Pat. No. 583,187. The tubular capsules are preferred because fine tubes can be coiled, twisted or otherwise deposited in various shapes to provide configurations that are appropriate for specific anatomical structures. Furthermore the tubular structure allows easy removal when needed. A detailed description of tubular capsule construction is disclosed in U.S. Pat, No. 5,283,187, which is incorporated herein by reference. Various polymers, such as polyacrylates (including acrilic copolymers) polyvinylidienes, polyurethahes, polystyrenes, polyamides, cellulose, acetates, celluose nitrates, polysulfones, polyacrylonitriles, as well as derivatives, copolymers, and mixtures thereof, can be used to form the membrane coatings of the capsules;

Many classes of compounds, when applied to the eye, are known to lower IOP. Examples include acetylcholine, epinephrine, prostaglandins, natriuretic peptides and endothelins (Kaufman, et al., "Medical Therapy of Glaucoma," Glaucoma, (eds.) P. L. Kaufman and T. W. Mittag, Mosby Publishing Co, pp. 9.7–9.30, 1991; Takashima, et al., "Effects of Natriuretic Peptide Family on Intraocular Pressure of Rabbit Eyes," Invest. Ophthalmol. Vis. Sci., 36: S734, 1995; and MacCumber, et al., "Ocular Effects of the Endothelins." Arch. Ophthalmol., 109:705–709, 1991). Thus, cells that naturally or are artificially transformed to secrete therapeutic amounts of these compounds will be useful in lowering IOP when encapsulated and implanted in the anterior chamber of the eye.

An example of cells naturally secreting IOP-lowering substance is the adrenal chromaffin celi, which is known to secrete epinephrine (Calve, et al., "Catecholarnine Secretion, Calcium Levels and Calcium Influx in Response to Membrane Depolarization in Bovine Chromaffin Cells," Neuroscience, 68:265–272, 1995; and Garcia, et al., "High-Performance Liquid Chromatographic Determination of Norepinephrine, Epinephrine, and Doparmine in Human Foetal Adrenal Gland." J. Chrontatogr B. Bionied. Appl., 656:77–80, 1994). Hence, bovine or human fetal adrenal chromaffin cells (or other epinephrine-secreting cells) encapsulated and implanted in the anterior chamber of the eye may be useful in the treatment of ocular hypertension. The amount of cells implanted should be sufficient to produce 0.1 to 100 $\mu$moles of epinephrine every day, preferably between 1 to 10 $\mu$moles day.

Another example of cells naturally secreting IOP-lowering substance is the endometrium epithelial cell, which is known to secrete a high amount of prostaglandin $F_{2a}$ (Kim. et al., "Cell Type Specificity and Protein Kinase C Dependency on the Stimulation of Prostaglandin $E_2$ and Prostaglandin $F_{2a}$ Production by Oxytocin and Platelet-Activating Factor in Bovine Endometrial Cell." J. Repiodiciion anid Fertility, 103:239–247, 1995). Hence, bovine endometrium epithelial cells (or other prostaglandin $F_{2a}$- secreting cells) encapsulated and implanted in the anterior chamber of the eye maybe useful in the treatment of ocular hypertension. The amount of cells implanted should be sufficient to produce 1 to 1000 nmoles of prostaglandin $F_{2a}$ every day, preferably between 10 to 100 nmoles/day.

For other IOP-lowering substances, where naturally secreting cells are not readily available, molecular biological techniques can be used to bioengineer an appropiate cell line to induce a continuous production and release of the compound of interest. For example a preferred compound of interest for IOP-lowering is acetylcholine. Acetylcholine is synthesized in the cell in a one-step reaction by choline acetyltransferase (ChAT; acetyl-CoA:choline O-acetyltransferase, EC 2.3.1.6). Stably transfected cells expressing ChAT cDNA will increase their acetylcholine synthesis and release. Numerous procedures are known to achieve the cloning and expression of cDNA and genomic DNA for ChAT in various cell lines. For example, Misawa and colleagues (Misawa, et al., "Calcium-Independent Release of Acetylcholine From Stable Cell Lines Expressing Mouse Choline Acewltransferase cDNA." *J. Neurochem.*, 62:465–470, 1994) demonstrated procedures for the construction of an expression vector for ChAT (pEFmChAT), which involved the insertion of the 2.7-kb EcoRI fragment with the whole protein-coding sequence of ChAT cDNA into the EcoRI site of vector pEF321A containing the promoter region for the human elongation is factor 1α. Transfection of tells with this expression factor was then performed by the modified calcium phosphate precipitation method using 10 μg of pEFmChAT and 2 μg pEFneo. Using this method, these investigators successfully and stably transfected six phenotypically different cell lines: NG108–15, NS20Y, N1E115, Neuro2A, L and NIH3T3 cells and showed that the transfected cells increased their synthesis and release of acetylcholine. Among these cells, the L cells are preferred because the greatest amount of acetylcholine was released from transfected L cells. Hence, pEFmChAT (or other vectors that increase the expression of ChAT)-transfected L cells (or other acetylcholine-secreting cells) encapsulated and implanted in the anterior chamber of the eye may be useful in the treatment of ocular hypertension. The amount of cells implanted should be sufficient to produce 0.1 to 100 μmoles of acetylcholine every day, preferably between 1 to 10 μmoles/day.

Using the same principle of gene expression, those who are skilled in the art can generate cells that synthesize, release or otherwise increase the effective concentration of IOP-lowering compounds such as prostaglandin $D_2$, endothelins (including endothelins-1, -2 and -3) and natriuretic peptides (including atrial natriuretic peptide, brain natriuretic peptide and C-type natriuretic peptide) or other IOP-lowering agents. For example, over-expression of prostaglandin D synthase, an enzyme responsible for the biosynthesis of prostaglandin $D_2$ (Urade. et al., "Prostaglandin D. E. F. Synthases," *J. Lipid Mediators Cell Signalling*, 12:257–273. 1995). whose cDNA sequence is known (Nagata, et al., "Human Brain Prostaglandin D Synthase Has Been Evolutionarily Differentiated From Lipophilic-Ligand Carrier Proteins." *Proc. NarlAcad. Sci. U.S.A.*, 88:4020–4024, 1991), will increase the basal production of prostaglandin $D_2$ by a suitable cell line. Thus, cell trasfected with vectors containing nucleotide sequences tha encode prostaglandin D synthase (or other postaglanding $D_2$ secreting cells) encapsulated and implanted in the anterior chamber of the eye may be useful in the treatment of ocular hypertension. The amount of cells implanted should be sufficient to produce 1 to 1000 nmoles of prostaglandin $D_2$ every day, preferably between 10 to 100 nmoles/day.

Similarly, the precursor of human endothelin-1, an IOP-lowering peptide, can be cloned and expressed and the product was shown to be functionally active (DiLella, et al., "Expression of Human Preproendothelin-1 cDNA in COS Cells Results in the Production of Mature Vasoactive Endothelin-1," *Biochem. Biophys. Res. Commun.*, 175:697–705, 1991). Thus, cells transfected with vectors containing nucleotide sequence that encode preproendothelin-1 (or other endothelin-1-secreting cells) encapsulated and implanted in the anterior chamber of the eye may be useful in the, treatment of ocular hypertention. Furthermore, functional endothelin-1 can be generated by proteolytic cleavage of inactive endothelin precursors (available in extacellular space) by an endothelin-converting enzyme. Hence, endothelin-converting enzyme is a key conponent in the biosynthesis pathway of the endothelins. Cloning and funtional expression of this enzyme can increase the production of functional endothelin-1 (Shimada, et al, "Cloning and Functional Expression of Human Endothelin-Converting Enzyme cDNA," *Biochenm. Btophys. Res. Commun.*, 207:807–812, 1995). Thus, cells transfected with vectors containing nucleotide sequences that encode endothelin-convering enzyme (or other cells naturaly secret this enzyme) encapsulated and implanted in the anterior chamber of the eye may be useful in the treatment of ocular hypertension. The amount of cells implanted should be sufficient to produce 1 to 1000 nmoles of functional endothelin-1 every day, preferably between 10 to 100 nmoles/day Natriuretic peptides, especially the C-type natriuretic peptide, can lower IOP. The gene and precursor structures of human C-type natriuretic peptide were characterized (Tawarage, et al., "Gene and Precursor Structures of Human C-type Natriuretic Peptide," *Biochem. Biophys. Res. Commun.*, 175:645–651, 1991; and Ogawa, et al., "Human C-Type Natriuretic Peptide: Characterization of the Gene and Peptide," *Hypertension*, 19:809–913, 1992). Those skilled in the art can use this information and clone and express this peptide in the appropriate cells. These cells transfected with vectors containing nucleotide sequences that encode C-type natriuretic peptide (or other cells naturally secret this peptide) encapsulated and implanted in the anterior chamber of the eye may be useful in the treatment of ocular hypertension. The amount of cells implanted should be sufficient to produce 1 to 1000 nmoles of C-type natriuretic peptide every day, preferably between 10 to 100 nmoles/day.

The above encapsulated cell that secrete IOP-lowering substances should be implanted in the anterior chamber, preferably surgically attached to the root of the iris adjacent to the trabecular meshwork, such that secreted compounds can quickly reach the trabecular meshwork and ciliary body.

I claim:

1. A method for lowering and controlling intraocular pressure comprising implanting in the anterior chamber of an eye and effective amount of encapsulated cells which secrete an intraocular pressure lowering substance selected from the group consisting of acetylcholine, epinephrine, prostaglandins, natriuretic peptides, and endothelins.

2. A capsule for implantation in the anterior chamber of an eye, encapsulating a cell, wherein said cell secretes through the capsule an intraocular pressure lowering substance selected from the group consisting of prostaglandins, natriuretic peptides and endothelins.

* * * * *

UNITED STATES PATENT AND TRADEMARK OFFICE
CERTIFICATE OF CORRECTION

PATENT NO. : 6,399,058 B1
DATED : June 4, 2002
INVENTOR(S) : Iok-Hou Pang

It is certified that error appears in the above-identified patent and that said Letters Patent is hereby corrected as shown below:

Title page,
Item [86], change "PCT/US99/17098" to -- PCT/US98/17098 --
Item [56], OTHER PUBLICATIONS, "Nathanson,..." reference, change "Atropetom" to -- Atriopeptin --.
"Misawa et al." reference, change "acetycholine" to -- acetylcholine --.

Column 1,
Line 16, change "TOP" to -- IOP --.
Line 23, change "methods," to -- methods --.
Line 32, change "95.8166" to -- 95/28166 --.
Line 36, change "9/0264A2" to -- 96/02646A2 --.

Column 2,
Line 15, change "583,187" to -- 5,283,187 --.
Line 23, change "acrilic" to -- acrylic --.
Line 24, change "polyurethahes" to -- polyurethanes --.
Line 25, change "celluose" to -- cellulose --.
Line 28, change "capsules;" to -- capsules. --
Line 44, change "celi," to -- cell, --.
Line 45, change "Catecholarnine" to -- Catecholamine --.
Line 50, change "Doparmine" to -- Dopamine --.
Line 51, change "Chrontatogr B. Bionied." to -- Chromatogr Biomed. --.
Lines 65-66, change "Repiodiciion anid" to -- Reproduction and --.

Column 3,
Line 2, change "maybe" to -- may be --.
Line 21, change "Acewltransferase" to -- acetyltransferase --.
Line 27, delete "is".
Line 28, change "tells" to -- cells --.
Line 56, change "1995)." to -- 1995), --.
Line 59, change "NatlAcad." to -- Natl. Acad. --.
Line 62, change "trasfected" to -- transfected --, change "tha" to -- that --.
Line 63, change "postaglanding" to -- prostaglandin --.

UNITED STATES PATENT AND TRADEMARK OFFICE
CERTIFICATE OF CORRECTION

PATENT NO. : 6,399,058 B1
DATED : June 4, 2002
INVENTOR(S) : Iok-Hou Pang

It is certified that error appears in the above-identified patent and that said Letters Patent is hereby corrected as shown below:

<u>Column 4,</u>
Line 11, change "the," to -- the --.
Line 16, change "conponent" to -- component --.
Line 17, change "funtional" to -- functional --.
Line 20, change "Biochenm." to -- Biochem. --.
Line 21, change "Btophys." to -- Biophys. --.
Line 23, change "convering enzime" to -- converting enzyme --.
Line 24, change "naturaly secret" to -- naturally secrete --.
Line 42, change "secret" to -- secrete --.
Line 48, change "cell" to -- cells --.

Signed and Sealed this

Third Day of June, 2003

JAMES E. ROGAN
*Director of the United States Patent and Trademark Office*